United States Patent
Suyker et al.

(10) Patent No.: US 7,022,127 B2
(45) Date of Patent: Apr. 4, 2006

(54) MECHANICAL ANASTOMOSIS SYSTEM FOR HOLLOW STRUCTURES

(75) Inventors: Wilhelmus Joseph Leonardus Suyker, Zwolla (NL); Paulus Thomas Wilhelmus Suyker, Amsterdam (NL)

(73) Assignee: Innovative Interventional Technologies BV, (NL)

( * ) Notice: Subject to any disclaimer, the term of this patent is extended or adjusted under 35 U.S.C. 154(b) by 191 days.

(21) Appl. No.: 10/405,677

(22) Filed: Apr. 1, 2003

(65) Prior Publication Data

US 2003/0195534 A1 Oct. 16, 2003

Related U.S. Application Data

(62) Division of application No. 10/162,261, filed on Jun. 4, 2002, which is a division of application No. 09/529,900, filed as application No. PCT/NL98/00605 on Oct. 22, 1998, now Pat. No. 6,485,496.

(30) Foreign Application Priority Data

Oct. 24, 1997 (NL) .................................... 1007349

(51) Int. Cl.
*A61B 17/04* (2006.01)
(52) U.S. Cl. .................................... 606/153
(58) Field of Classification Search ................. 606/153
See application file for complete search history.

(56) References Cited

U.S. PATENT DOCUMENTS

| | | | |
|---|---|---|---|
| 1,251,258 A | 12/1917 | Magill |
| 1,756,670 A | 4/1930 | Treat |
| 1,918,890 A | 7/1933 | Bacon |
| 2,434,030 A | 1/1948 | Yeomans |
| 2,453,056 A | 11/1948 | Zack |
| 2,707,783 A | 5/1955 | Sullivan |
| 3,040,748 A | 6/1962 | Klein et al. |
| 3,080,564 A | 3/1963 | Strekopitov et al. |
| 3,193,165 A | 7/1965 | Akhalaya et al. |
| 3,217,557 A | 11/1965 | Martinot |
| 3,252,643 A | 5/1966 | Strekopytov et al. |
| 3,254,650 A | 6/1966 | Collito |
| 3,254,651 A | 6/1966 | Collito |
| 3,269,630 A | 8/1966 | Fleicher |
| 3,388,847 A | 6/1968 | Kasulin et al. |

(Continued)

FOREIGN PATENT DOCUMENTS

DE 28 22 603 A1 5/1978

(Continued)

OTHER PUBLICATIONS

Ann Thorac Surg, Assessment of Patented Coronary End-To-Side Anastomotic Devices Using Micromechanical Bonding, Department of Design, Engineering and PRoduction, Delft University of Technology, The Netherlands, Jul. 2000; 70(1) :218-21.

(Continued)

*Primary Examiner*—Gary Jackson
(74) *Attorney, Agent, or Firm*—Knoble, Yoshida & Dunleavy, LLC

(57) ABSTRACT

A system for making anastomoses between hollow structures by mechanical means is provided with a device in the shape of an annular or tubular element comprising circumferentially provided means, such as pin-shaped elements, for joining the abutting walls of the hollow structures together. An applicator is intended for moving said annular or tubular element in position and activating the joining means thereof, so as to make the anastomosis. Possibly, intraluminal joining means can be inserted without using an annular or tubular element.

9 Claims, 15 Drawing Sheets

U.S. PATENT DOCUMENTS

| | | | |
|---|---|---|---|
| 3,452,615 A | 7/1969 | Gregory | |
| 3,494,533 A | 2/1970 | Green et al. | |
| 3,519,187 A | 7/1970 | Kapitanov | |
| 3,552,626 A | 1/1971 | Astafiev et al. | |
| 3,570,497 A | 3/1971 | Lemole | |
| 3,589,589 A | 6/1971 | Akopov | |
| 3,593,903 A | 7/1971 | Astafiev et al. | |
| 3,638,652 A | 2/1972 | Kelley | |
| 3,657,744 A | 4/1972 | Ersek | 3/1 |
| 3,692,224 A | 9/1972 | Astafiev et al. | |
| 3,774,615 A | 11/1973 | Lim et al. | |
| 3,805,793 A | 4/1974 | Wright | |
| 3,908,662 A | 9/1975 | Razgulov et al. | |
| 4,076,162 A | 2/1978 | Kapitanov et al. | |
| 4,140,126 A | 2/1979 | Choudhury | |
| 4,166,466 A | 9/1979 | Jarvik | |
| 4,214,587 A | 7/1980 | Sakura | 128/334 |
| 4,233,981 A | 11/1980 | Schomacher | |
| 4,304,236 A | 12/1981 | Conta et al. | |
| 4,319,576 A | 3/1982 | Rothfuss | |
| 4,325,376 A | 4/1982 | Klieman et al. | |
| 4,350,160 A | 9/1982 | Koslesov et al. | |
| 4,351,466 A * | 9/1982 | Noiles | 227/8 |
| 4,352,358 A | 10/1982 | Angelchik | |
| 4,366,819 A | 1/1983 | Kaster | |
| 4,368,736 A | 1/1983 | Kaster | 128/334 |
| 4,466,436 A | 8/1984 | Lee | |
| 4,505,414 A | 3/1985 | Filipi | 227/19 |
| 4,523,592 A | 6/1985 | Daniel | |
| 4,553,542 A | 11/1985 | Schenck et al. | |
| 4,573,468 A | 3/1986 | Conta et al. | |
| 4,576,167 A | 3/1986 | Noiles | |
| 4,586,503 A | 5/1986 | Kirsch et al. | |
| 4,592,354 A | 6/1986 | Rothfuss | |
| 4,593,693 A | 6/1986 | Schenck | |
| 4,603,693 A | 8/1986 | Conta et al. | |
| 4,607,637 A | 8/1986 | Berggren et al. | |
| 4,624,255 A | 11/1986 | Schenck et al. | |
| 4,624,257 A | 11/1986 | Berggren et al. | |
| 4,646,745 A | 3/1987 | Noiles | |
| 4,657,019 A | 4/1987 | Walsh et al. | |
| 4,665,906 A | 5/1987 | Jervis | |
| 4,681,110 A | 7/1987 | Wiktor | 128/343 |
| 4,700,703 A | 10/1987 | Resnick et al. | 128/334 |
| 4,703,887 A | 11/1987 | Clanton et al. | |
| 4,747,407 A | 5/1988 | Liu et al. | |
| 4,800,882 A | 1/1989 | Gianturco | |
| 4,872,874 A | 10/1989 | Taheri | 623/1 |
| 4,907,591 A | 3/1990 | Vasconcellos et al. | |
| 4,917,087 A | 4/1990 | Walsh et al. | |
| 4,917,090 A | 4/1990 | Berggren et al. | |
| 4,917,091 A | 4/1990 | Berggren et al. | |
| 4,957,499 A | 9/1990 | Lipatov et al. | |
| 5,035,702 A | 7/1991 | Taheri | 606/153 |
| 5,064,435 A | 11/1991 | Porter | |
| 5,102,417 A | 4/1992 | Palmaz | |
| 5,104,399 A | 4/1992 | Lazarus | 623/1 |
| 5,119,983 A | 6/1992 | Green et al. | |
| 5,177,112 A | 1/1993 | Horn | 514/654 |
| 5,188,638 A | 2/1993 | Tzakis | |
| 5,197,649 A | 3/1993 | Bessler et al. | |
| 5,234,447 A | 8/1993 | Kaster et al. | 606/153 |
| 5,234,456 A | 8/1993 | Silvestrini | |
| 5,242,457 A | 9/1993 | Akopov et al. | |
| 5,250,058 A | 10/1993 | Miller et al. | |
| 5,256,661 A | 10/1993 | Horn | 514/248 |
| 5,258,042 A | 11/1993 | Mehta | |
| 5,271,543 A | 12/1993 | Grant et al. | |
| 5,292,053 A | 3/1994 | Bilotti et al. | |
| 5,304,220 A | 4/1994 | Maginot | |
| 5,324,447 A | 6/1994 | Lam et al. | |
| 5,330,503 A | 7/1994 | Yoon | |
| 5,333,773 A | 8/1994 | Main et al. | |
| 5,336,233 A | 8/1994 | Chen | |
| 5,348,259 A | 9/1994 | Blanco et al. | |
| 5,366,462 A | 11/1994 | Kaster et al. | |
| 5,366,473 A | 11/1994 | Winston et al. | |
| 5,387,235 A | 2/1995 | Chuter | 623/1 |
| 5,395,030 A | 3/1995 | Kuramoto et al. | |
| 5,397,345 A | 3/1995 | Lazarus | 128/898 |
| 5,397,355 A | 3/1995 | Marin et al. | 623/1.2 |
| 5,403,333 A | 4/1995 | Kaster et al. | |
| 5,456,714 A | 10/1995 | Owen | |
| 5,478,354 A | 12/1995 | Tovey et al. | |
| 5,489,295 A | 2/1996 | Piplani et al. | |
| 5,522,834 A | 6/1996 | Fonger et al. | |
| 5,549,619 A | 8/1996 | Peters et al. | |
| 5,554,162 A | 9/1996 | DeLange | |
| 5,562,690 A | 10/1996 | Green et al. | 606/154 |
| 5,562,728 A | 10/1996 | Lazarus et al. | |
| 5,620,452 A | 4/1997 | Yoon | |
| 5,634,936 A | 6/1997 | Linden et al. | |
| 5,695,504 A | 12/1997 | Gifford, III et al. | 606/153 |
| 5,707,380 A | 1/1998 | Hinchliffe et al. | 606/163 |
| 5,709,335 A | 1/1998 | Heck | |
| 5,720,776 A | 2/1998 | Chuter et al. | |
| 5,732,872 A | 3/1998 | Bolduc et al. | 227/176.1 |
| 5,755,775 A | 5/1998 | Trerotola et al. | |
| 5,755,777 A | 5/1998 | Chuter | |
| 5,797,933 A | 8/1998 | Snow et al. | 606/151 |
| 5,833,698 A | 11/1998 | Hinchliffe et al. | 606/153 |
| 5,839,639 A | 11/1998 | Sauer | |
| 5,843,164 A | 12/1998 | Frantzen et al. | |
| 5,843,170 A | 12/1998 | Ahn | |
| 5,868,760 A | 2/1999 | McGuckinns et al. | |
| 5,868,763 A | 2/1999 | Spence et al. | 606/153 |
| 5,879,380 A | 3/1999 | Kalmann et al. | |
| 5,881,943 A | 3/1999 | Heck et al. | |
| 5,904,697 A | 5/1999 | Gifford, III et al. | |
| 5,906,607 A | 5/1999 | Taylor et al. | |
| 5,927,284 A | 7/1999 | Borst et al. | |
| 5,931,842 A | 8/1999 | Goldsteen et al. | 606/108 |
| 5,951,576 A | 9/1999 | Wakabayashi | |
| 5,976,159 A | 11/1999 | Bolduc et al. | 606/142 |
| 5,976,176 A | 11/1999 | Webb, II | |
| 5,976,178 A | 11/1999 | Goldsteen et al. | 623/1 |
| 6,015,378 A | 1/2000 | Borst et al. | |
| 6,019,722 A | 2/2000 | Spence et al. | |
| 6,032,672 A | 3/2000 | Taylor | |
| 6,036,702 A | 3/2000 | Bachinski et al. | 606/153 |
| 6,051,007 A | 4/2000 | Hogendijk et al. | |
| 6,063,021 A | 5/2000 | Hossain et al. | |
| 6,066,148 A | 5/2000 | Rygaard | 606/153 |
| 6,071,235 A | 6/2000 | Furnish et al. | |
| 6,074,416 A | 6/2000 | Berg et al. | 623/1 |
| 6,080,175 A | 6/2000 | Hogendijk | |
| 6,095,997 A | 8/2000 | French et al. | |
| 6,110,187 A | 8/2000 | Donlon | |
| 6,110,188 A | 8/2000 | Narciso, Jr. | |
| 6,113,588 A | 9/2000 | Duhaylongsod et al. | |
| 6,113,612 A * | 9/2000 | Swanson et al. | 623/1.15 |
| 6,139,492 A | 10/2000 | Vierra et al. | |
| 6,152,937 A | 11/2000 | Peterson et al. | |
| 6,165,196 A | 12/2000 | Stack et al. | |
| 6,176,864 B1 | 1/2001 | Chapman | |
| 6,190,353 B1 | 2/2001 | Makower et al. | |
| 6,193,734 B1 | 2/2001 | Bolduc et al. | |
| D440,304 S | 4/2001 | Morales | |
| 6,241,741 B1 | 6/2001 | Duhaylongsod et al. | |
| 6,485,496 B1 | 11/2002 | Suyker et al. | 606/153 |
| 6,602,263 B1 | 8/2003 | Swanson et al. | 606/153 |
| 6,616,675 B1 | 9/2003 | Evard et al. | |
| 6,702,829 B1 | 3/2004 | Bachinski et al. | |
| 2002/0183769 A1 | 12/2002 | Swanson et al. | 606/153 |

FOREIGN PATENT DOCUMENTS

| | | |
|---|---|---|
| DE | 2822603 | 11/1979 |
| DE | 195 42 733 A1 | 11/1995 |
| DE | 19542733 | 7/1997 |
| EP | 0 119 688 | 9/1984 |
| EP | 0 384 647 | 8/1990 |
| EP | 0419 660 | 3/1991 |
| EP | 0 539 237 A1 | 10/1992 |
| EP | 0 637 454 | 2/1995 |
| EP | 137685 | 4/1995 |
| EP | 0 689 806 | 1/1996 |
| EP | 0 712 614 | 5/1996 |
| EP | 0 820 724 B1 | 7/1997 |
| EP | 0 820 725 B1 | 7/1997 |
| EP | 0 885 595 A1 | 6/1998 |
| FR | 1518083 | 12/1968 |
| GB | 935490 | 9/1959 |
| GB | 2038692 | 7/1980 |
| GB | 2108418 | 5/1986 |
| NL | 7711347 | 4/1979 |
| SU | 995765 | 2/1983 |
| SU | 1097301 | 6/1984 |
| WO | WO 89/08433 | 9/1989 |
| WO | WO 95/17127 | 6/1995 |
| WO | 96/10375 | 4/1996 |
| WO | 96/14808 | 5/1996 |
| WO | 98/02099 | 1/1998 |
| WO | WO 98/19608 | 5/1998 |
| WO | WO 98/19618 | 5/1998 |
| WO | WO 98/19629 | 5/1998 |
| WO | WO 98/19630 | 5/1998 |
| WO | WO 98/19631 | 5/1998 |
| WO | WO 98/19632 | 5/1998 |
| WO | WO 98/19634 | 5/1998 |
| WO | WO 98/19732 | 5/1998 |
| WO | WO 98/55027 A2 | 5/1998 |
| WO | WO 98/55027 A3 | 5/1998 |
| WO | WO 98/47430 | 10/1998 |
| WO | WO 99/21491 A1 | 10/1998 |
| WO | WO 98/5027 | 12/1998 |
| WO | WO 98/55027 | 12/1998 |
| WO | WO 99/38454 A2 | 12/1998 |
| WO | WO 00/27313 A3 | 5/1999 |
| WO | WO 00/27313 | 5/2000 |
| WO | 00/53104 | 9/2000 |
| WO | 00/74579 | 12/2000 |

OTHER PUBLICATIONS

Werker et al, "Review of Faciitated Approaches To Vascular Anastomosis Surgery", Department of Plastic, REconstructive and Hand Surgery, University Hospital Utrecht, Utrecht, the Netherlands, 1997: 63:5127.

Androsov, "New Method of Surgical Treatment of Blood Vessel Lesions," Arch. Surg. 1956;73:262-265.

Berggren et al., "Clinical Experience with UNILINK 3M Precise Microvascular Anastomotic Device," Scand J Plast Reconstr Hand Surg. 1993;27;35-39.

CALAFIORE, A.m., "Early Clinical Experience With a New Sutureless Anastomotic Device for Proximal Anastomosis of the Saphenous Vein to the Aorta," The Journal of Thoracic and Cardiovascular Surgery, vol. 121, No. 5, pp. 854-858, May 2001.

Cooper et al., "Development of the Surgical Stapler with Emphasis on Vascular Anastomosis," NY Acad. Sci. 1963;25:365-377.

Eckstein, f.s., et al., Sutureless Mechanical Anastomosis of a Saphenous Vein Graft to a Coronary Artery With a New Connector Device, The Lancet pp. 931-932 vol. 357 Mar. 24, 2001.

Gentili et al., "A Technique for Rapid Non-suture Vascular Anastomosis," Can J Neuro Sci, 1987;14(1):92-95.

Goetz et al., "Internal Mammary-coronary Artery Anastomosis: A Nonsuture Method Employing Tantalum Rings," J Thorac Card Surg. 1961;41(3);378-386.

Gottlob et al., "Anastomoses of Small Arteries and Veins by Means of Bushings and Adhesive," J Card Surg, 1968;9:337-341.

Guyton et al., "A Mechanical Device for Sutureless Aorta—Saphenous Vein Anastomosis," Ann Thorac Surg, 1979;28:342-345.

Holt et al., "A New Method for Microvascular Anastomosis: Report of Experimental and Clinical Research," The American Surgeon 1992;58(12);722-727.

Holt et al., "A New Technique for End-to-end Anastomosis of Small Arteries," Surg Forum, 1960;11:242.

Inokuchi, "A New Type of Vessel-suturing Apparatus," AMA Arch Surg, 1958;77:954-957.

Inokuchi, "Stapling Device for End-to-side Anastomosis of Blood Vessels," Arch Surg, 1961;82:27-31.

Kirsch et al., "A New Method for Microvascular Anastomosis: Report of Experimental and Clinical Research," American Surgeon 1992;58;722-727.

Schumacker et al., "A New Technique for End-to-end Anastomosis of Small Arteries," Surgical Forum, 1960;11:242-243.

Lanzetta et al., "Long-term Results of 1 Millimeter Arterial Anastomosis Using the 3M Precise Microvascular Anastomotic System" Microsurgery 1992;13;313-320.

Li et al., "End-to-side-anastomosis in the Dog Using the 3M Precise Microvascular Anastomotic System: A Comparative Study," I. Reconstruct. Microsurg. 1991;7(4);345-350.

Miller, "The Russian Stapling Device," Acad Sci, 1963;25:378-381.

Nakayama et al., "A Simple New Apparatus for Small Vessel Anastomosis (free autograft of the sigmoid included)," Surgery, 1962;52(8);918-931.

Narter et al., "An Experimental Method for Nonsuture Anastomosis of the Aorta," Surg Gyne & Obs, 1964;632-361.

Nazari et al., "Expandable Prosthesis for Sutureless Anastomosis in Thoracic Aorta Prosthetic Substitution", European Journal of Cardiothoracic Surgery vol. 10 No. 11 1996 pp. 1003-1009.

Olearchyk, "Vasilii I. Kolesov—A Pioneer of Coronary Revascularization by Internal Mammary-coronary Artery Grafting," J Thorac Surg. 1998;98(1);13-18.

Ragnarsson et al., "Arterial End-to-side Anastomosis with the UNILINK System," Ann Plastic Surg, 1989;22(3):405-415.

Ragnarsson et al, "Microvenous End-to-side Anastomosis: An experimental Study Comparing the UNILINK System and Sutures" I. ReconstructMicrosurg. 1989; 5(3):217-224.

Rohman et al., Chapter IX—Cardiovascular Technique, "Double Coronary Artery-internal Mammary Artery Anastomoses, Tantalum Ring Technique" Surg. Forum 1960;11;236-243.

J. Rosch et al., "Modified Gianturco Expandable Wire Stents in Experimental and Clincial Use", Annals of Radiology, 1998, 31, 2 pp. 100-104.

Vogelfanger et al., "A Concept of Automation in Vascular Surgery: A Preliminary Report on a Mechanical Instrument for Arterial Anastomosis" Can.I. Surg. 1958;58; 262-265.

* cited by examiner

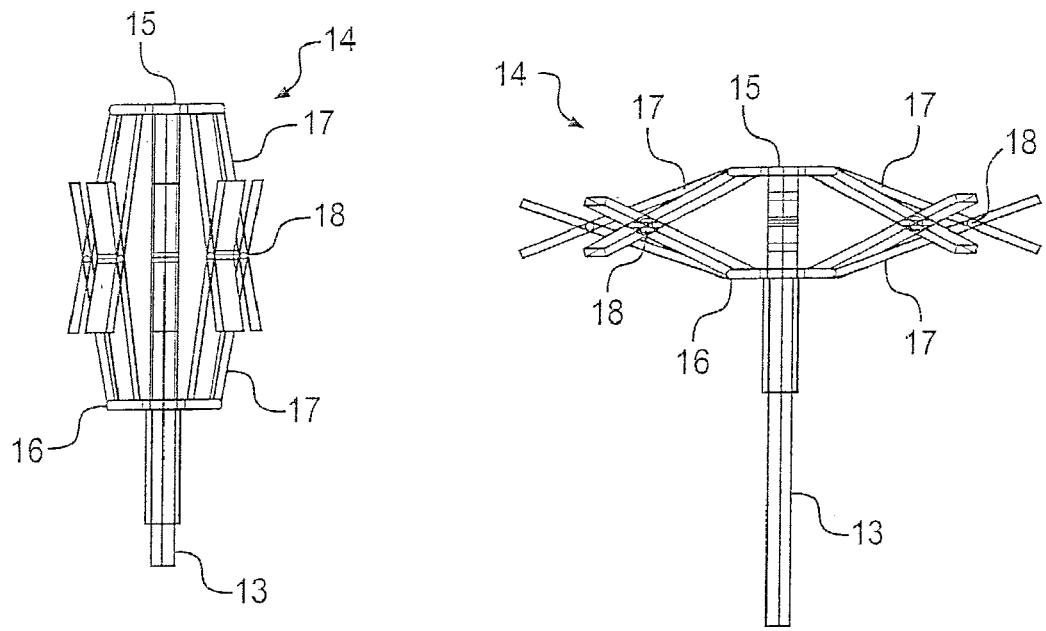
FIG. 13
FIG. 15
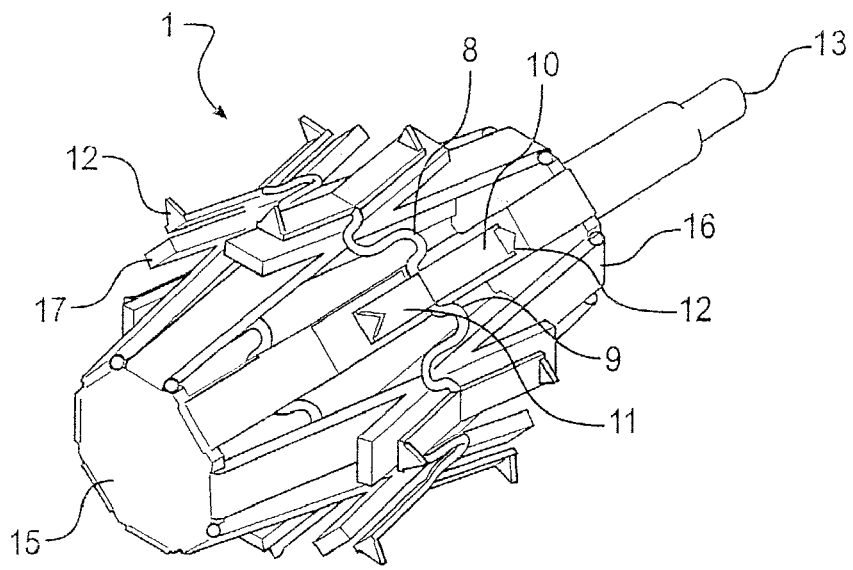
FIG. 14

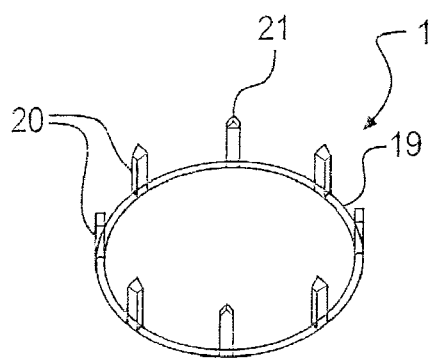
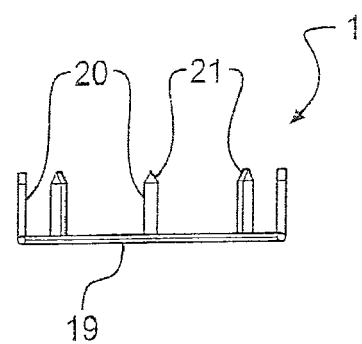
FIG. 16   FIG. 17
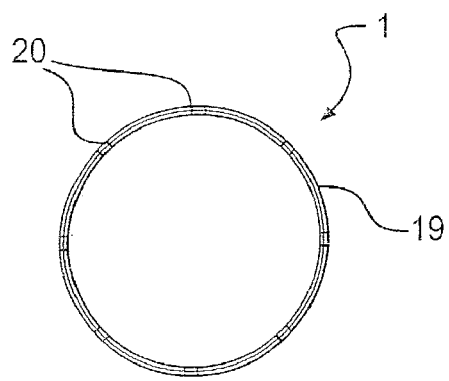
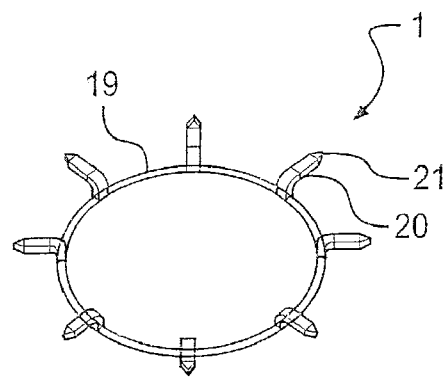
FIG. 18   FIG. 19
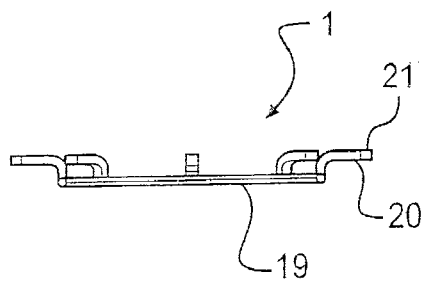
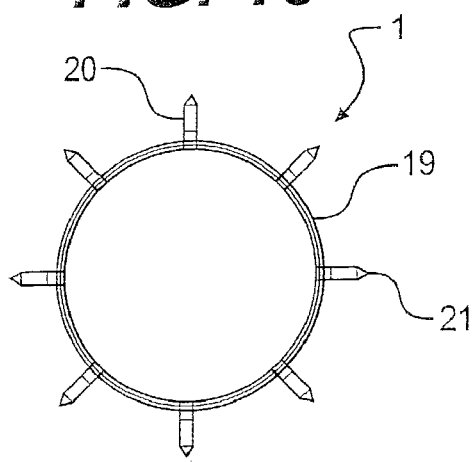
FIG. 20   FIG. 21

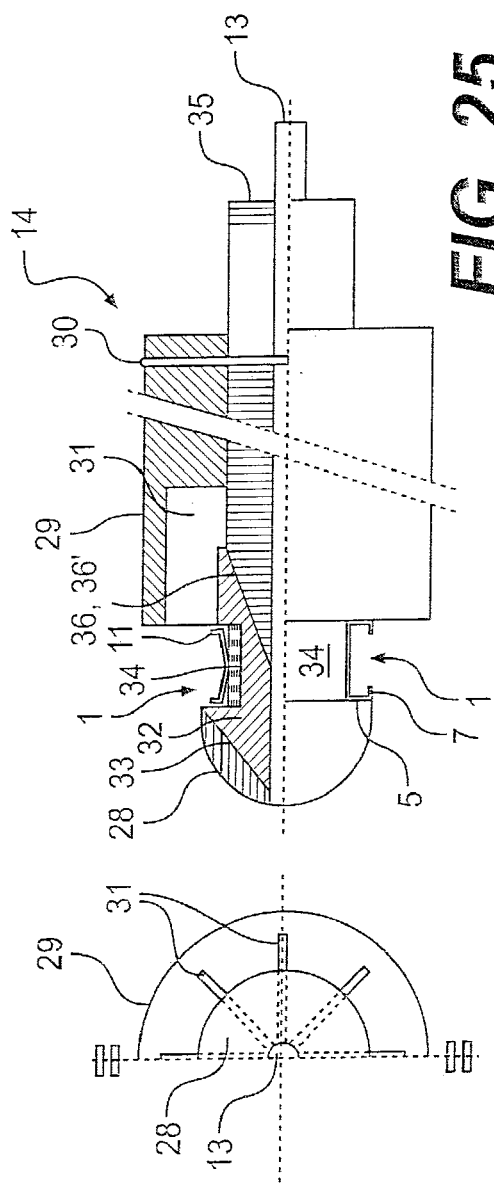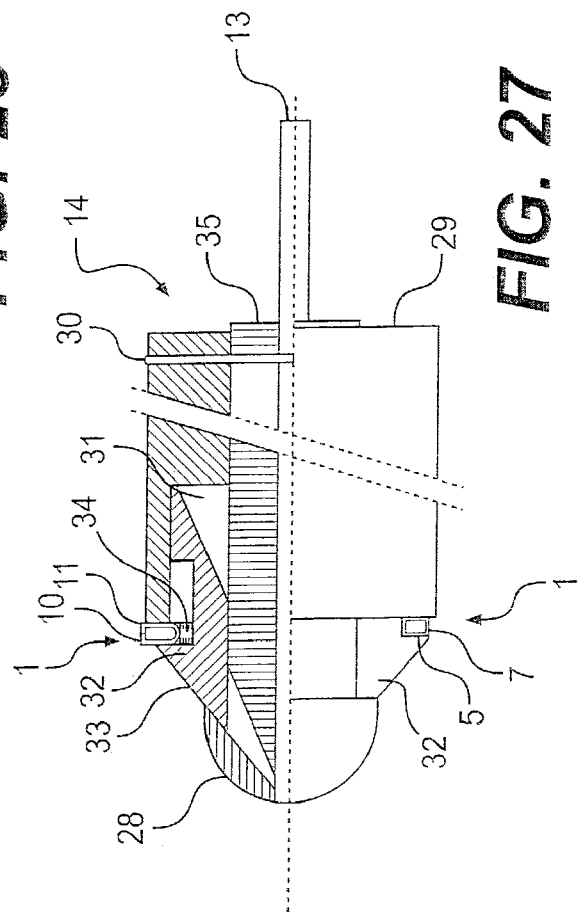

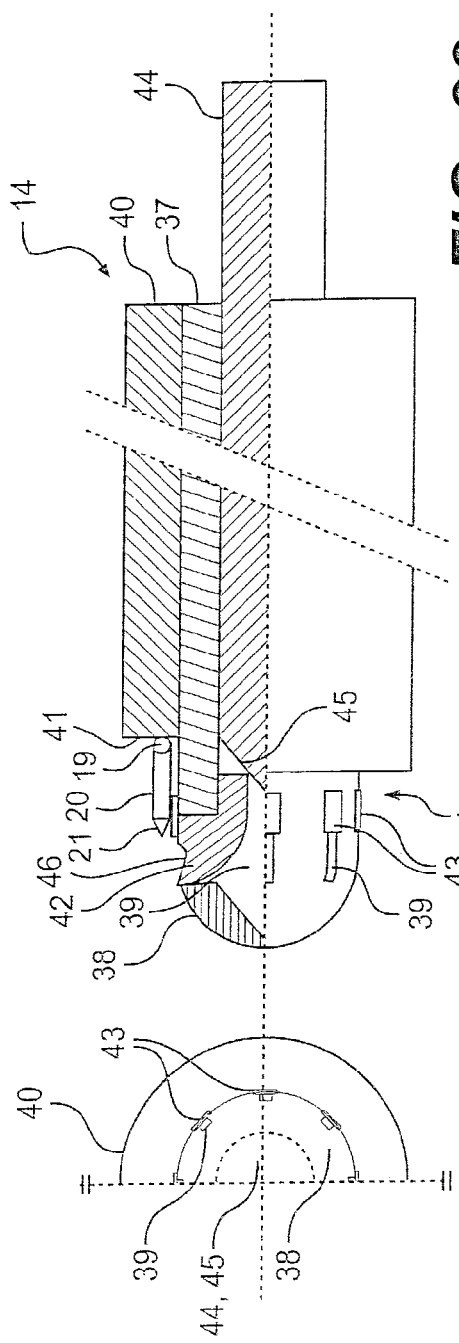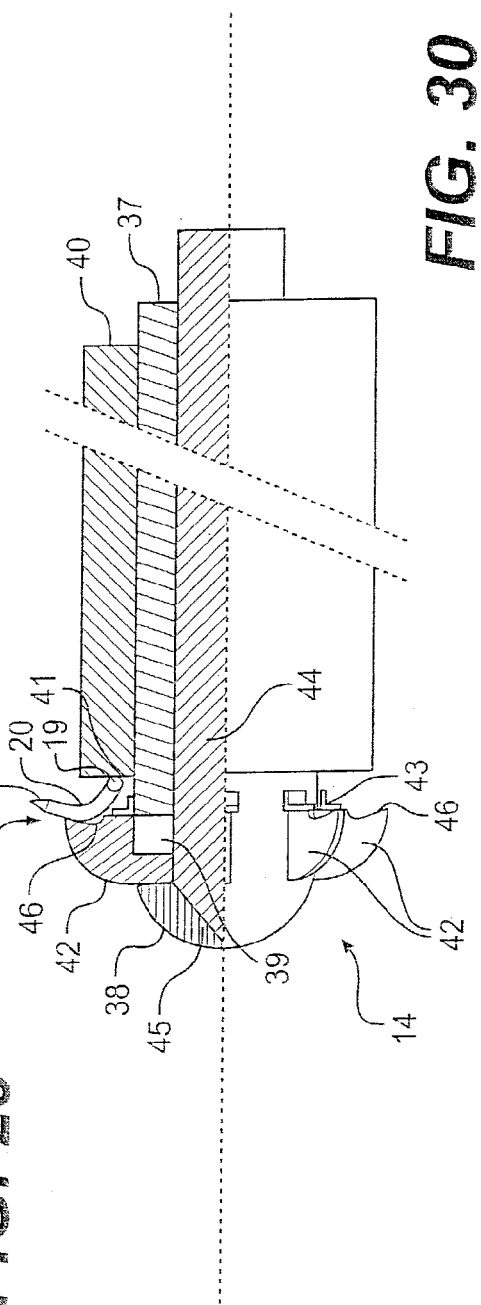

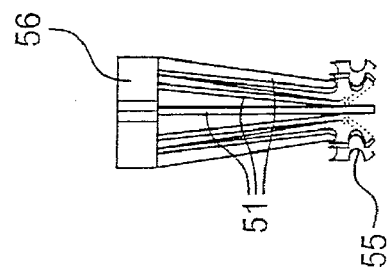
FIG. 34
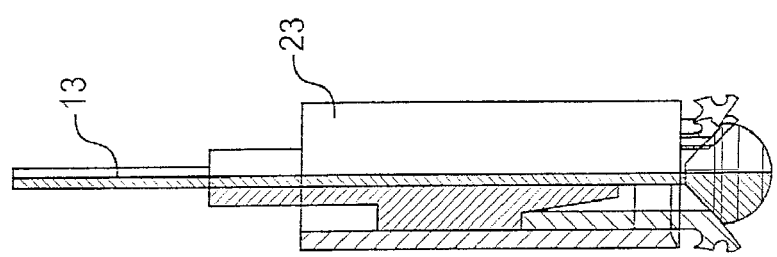
FIG. 33
FIG. 32
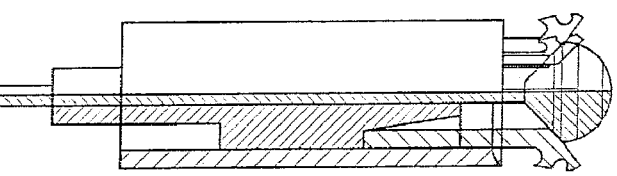
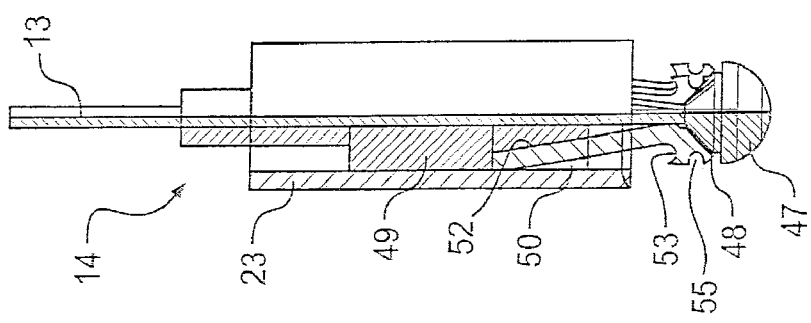
FIG. 31

MECHANICAL ANASTOMOSIS SYSTEM FOR HOLLOW STRUCTURES

This application is a divisional of U.S. patent application Ser. No. 10/162,261, filed on Jun. 4, 2002, currently pending, which is a divisional of U.S. application Ser. No. 09/529,900, filed Apr. 21, 2000, now U.S. Pat. No. 6,485, 496 issued Nov. 26, 2002 which is a 371 of PCT/NL98/00605, filed Oct. 22, 1998.

The present invention relates to a system for making anastomoses between hollow structures by mechanical means, and also to a device and an applicator for use therewith.

Such a system may for example be used when making a bypass past narrowings or occlusions of arteries caused by arteriosclerosis. There are now various possibilities of remedying such constrictions or occlusions.

If the constriction or occlusion takes place in a coronary artery, the least radical method is to dilate the constriction by means of a PTCA procedure (Percutaneous Transluminal Coronary Angioplasty), which may or may not be followed by the placing or an intraluminal stent. This is not always possible, however.

On the other hand, as already mentioned before, it is possible to make a bypass by means of surgery. To this end an artery (arteria mammaria interna) or a vein from the leg (vena saphena magna) may be used, for example. An anastomosis is thereby made in the coronary artery, distally of the constriction or occlusion. The interconnection between the vessels is then manually sutured by means of 8 to 20 stitches. Said anastomosis may be a side-to-side or an end-to-side anastomosis. The natural origin of the arteria mammaria interna is usually preserved, so that such a bypass will directly be functional. A bypass made of a vena saphena magna will have to be sutured separately in the aorta (the so-called proximal anastomosis). Due to the small diameter of coronary arteries (1–3 mm), it is generally decided to stop the heart in order to be able to carry out the anastomosis precisely and safely. The blood circulation is kept going by a heart-lung machine during this time. Although this is a well-tried and reasonably safe method, it has certain drawbacks. Thus, the use of the heart-lung machine has a number of side effects for the patient, as a result of which recovery following surgery takes more time. Moreover, the necessary disposables for the heart-lung machine are costly.

At present, techniques are available for a number of readily accessible coronary arteries to make manually sutured vascular connections to a beating, functioning heart. Generally, a device which more or less immobilizes a small area of the heart by mechanical means is used thereby. The drawbacks of said method are the fact that only a limited number of places on the heart can be reached and the fact that part of the heart is temporarily anaemic, because it is necessary to stop the circulation through the blood vessel to be treated for 8–15 minutes.

The object of the present invention is to provide a system for making anastomoses between hollow structures by mechanical means, which will make it easier to make mechanical anastomoses.

In order to accomplish that objective, the system according to the invention is characterized by a device in the shape of an annular or tubular element comprising joining means provided circumferentially thereon for joining the abutting walls of the hollow structures together, as well as an applicator for moving said annular or tubular element in position and activating the joining means thereof.

The system according to the invention makes it possible to effect an anastomosis faster and more easily by placing an annular or tubular element comprising joining means with the aid of said applicator, which joining means are also activated by said applicator, in such a manner that the anastomosis is made.

The system according to the invention has a wide range of applications, due to the fast and accurate manner of making an anastomosis. Thus, the following applications are conceivable:

"port access surgery", such as laparoscopic or thoracoscopic vascular reconstructions;

small, precise vascular connections to a moving organ, as in heart surgery; and vascular reconstructions wherein the circulation through the supplying vessel may only be shut off for a very short period of time, as in neurosurgery.

Of course, it is also possible to use the invention to make anastomoses between other hollow structures.

The invention also comprises embodiments of devices and applicators for use in the above-described system for making anastomoses by mechanical means.

The device of the system according to the invention can be used intraluminally as well as extraluminally, and it can be adapted both for side-to-side anastomoses and for end-to-side anastomoses. The joining means are preferably pin-shaped elements, whereby pairs of pin-shaped elements may be considered, which can function as staples, or independently operating pin-shaped elements, which can be fixed to the vessel walls by being deflected. Preferably, the tubular or annular elements for intraluminal use can expand from a smaller starting diameter to a final joining diameter, whereby the joining means can be activated either automatically upon expansion or individually. The elements may have a circular cross-section, but also an elliptical cross-section, for example, so that the resulting anastomosis will also have a circular or an elliptical cross-section.

The invention furthermore comprises a method for making intraluminal side-to-side or side-to-end anastomoses between hollow structures by mechanical means, which is characterized by providing an applicator and associated joining means for joining the abutting walls of the hollow structures together, placing said joining means round the applicator, inserting said applicator and said joining means into one of said hollow structures to a location internally of the abutting walls of the hollow structures, and activating said applicator, and thus passing said joining means through said abutting walls or clamping said joining means against said abutting walls for the purpose of keeping said abutting walls in sealing contact with each other.

With this method, a number of loose staples may be used as the joining means.

The invention will be explained in more detail hereafter with reference to the drawings, which show embodiments of the invention.

Figure 3:
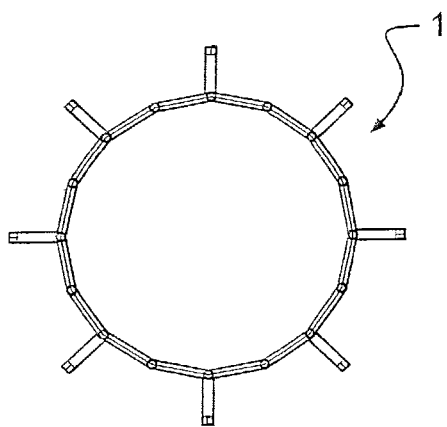
FIG. 3 is an axial view of the device according to FIG. 1.
Figure 3A:
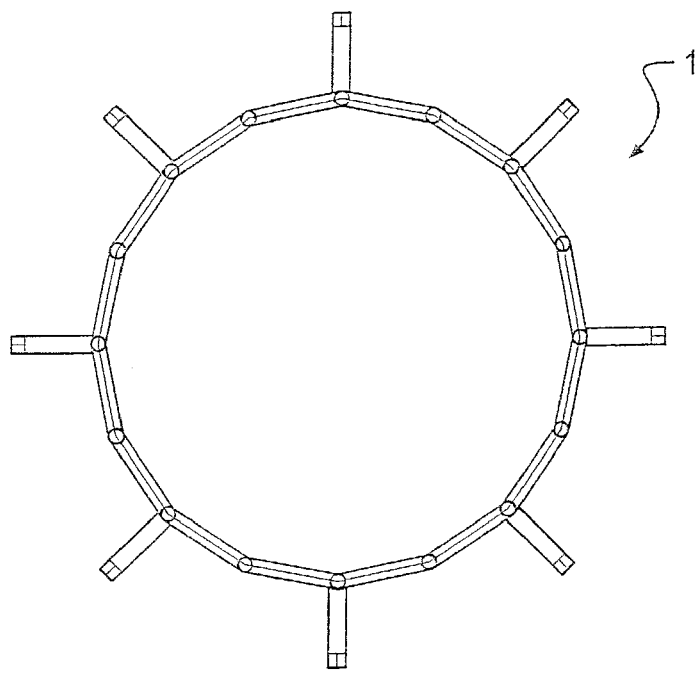
FIG. 3a shows an axial view of a device similar to that shown in FIG. 3 except which has an elliptical cross-section.
Figure 6A:
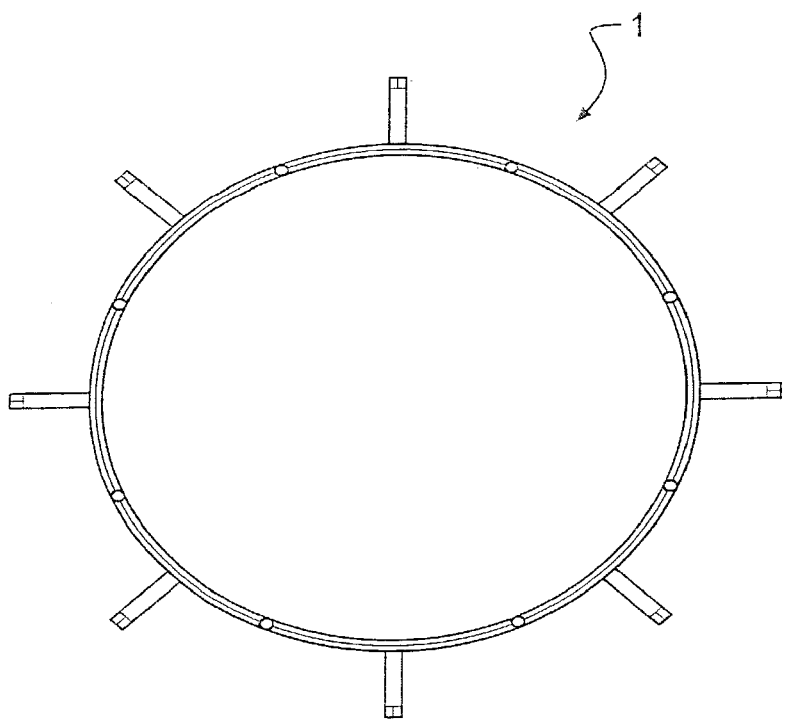
FIGS. 5 and 6 are a side view and an axial view, respectively, of the device of FIG. 4.

FIG. 6*a* shows an axial view of the device of FIG. 3*a* in the joining position.

FIGS. 7–12 are views corresponding with FIGS. 1–6 of a second embodiment of the device according to the invention. From the axial views shown in FIGS. 9 and 12, it can be seen that the second embodiment of the device according to the invention has a polygonal cross-section.

FIG. 13 is a side view of an applicator for use with the device according to FIGS. 7–12, showing the starting position thereof.

FIG. 14 is a perspective view of the applicator of FIG. 13, with the device according to FIGS. 7–12, which is shown in the starting position thereof, in mounted position thereon.

FIG. 15 is a side view corresponding with FIG. 13, wherein the applicator is shown in the joining position, however.

FIGS. 16–21 are views corresponding with FIGS. 1–6 of a third embodiment of the device according to the invention.

Figure 22:
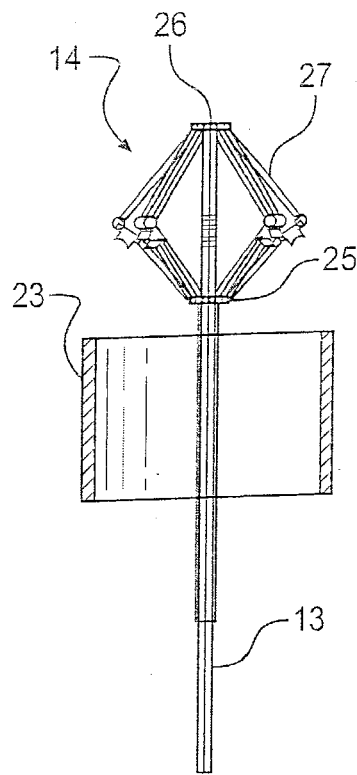
Figure 24:
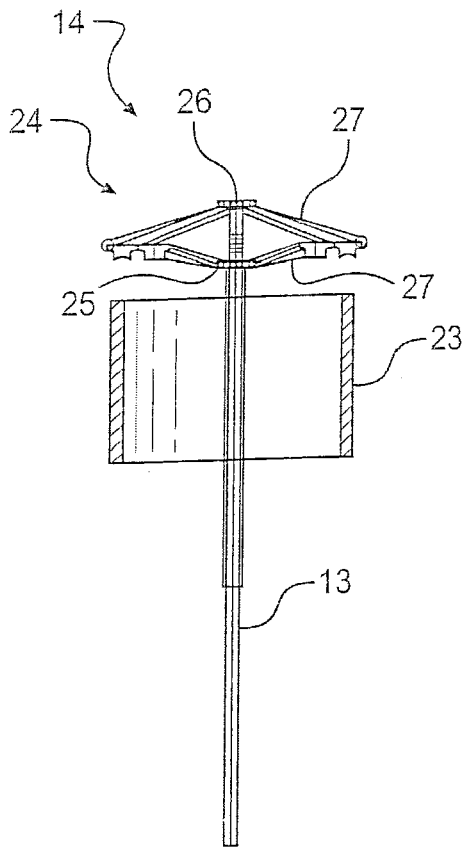
Figure 23:
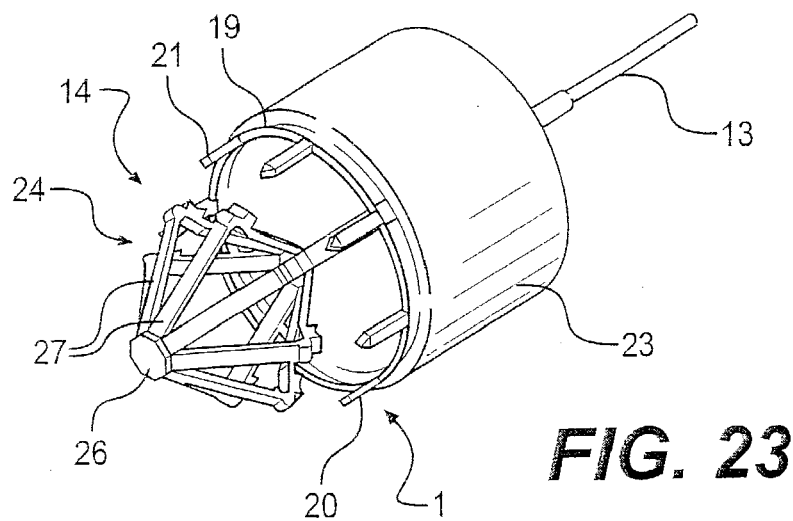

FIGS. 22–24 are views corresponding with FIGS. 13–15 of an applicator for use with the device according to FIGS. 16–21.

FIG. 25 is a schematic side view, partially in sectional view, of an alternative applicator for use with the device according to FIGS. 1–6 or 7–12.

FIG. 26 is a partial front view of the applicator of FIG. 25.

FIG. 27 is a view corresponding with FIG. 25, wherein the applicator is shown in the expanded position, however.

FIGS. 28–30 are sectional views and elevational views respectively corresponding with FIGS. 25–27 of a variant of an applicator for use with a device according to FIGS. 16–21.

FIGS. 31–33 are partially cut-away side views of another variant of the applicator, for example for use with a device according to FIGS. 1–6 or 7–12, showing three different positions thereof.

FIG. 34 is a side view of a variant of the extendible arms of the applicator of FIG. 31.

Figure 35:
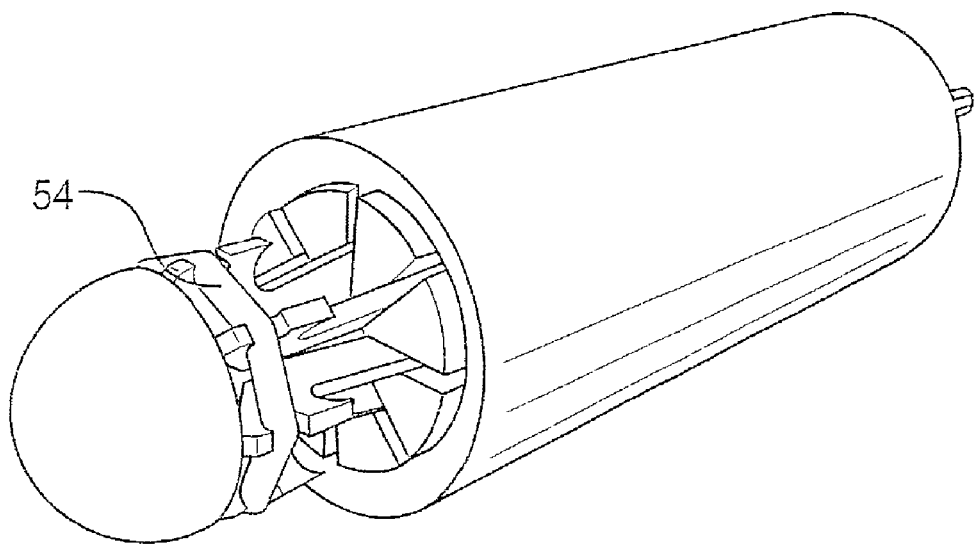
Figure 36:
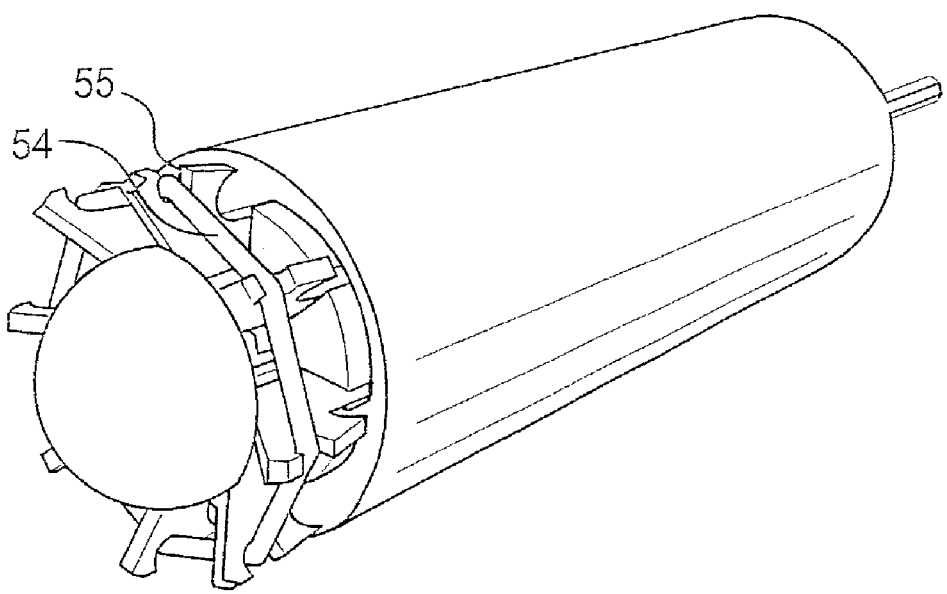

FIGS. 35, 36 are perspective views of the applicator of FIG. 31, showing the two extreme positions thereof.

FIGS. 37, 38 and 39, 40 are side views and perspective views, respectively, of yet another variant of the applicator according to the invention for use with a device according to FIGS. 1–6 or 7–12, for example, showing the two extreme positions thereof.

Figure 41:
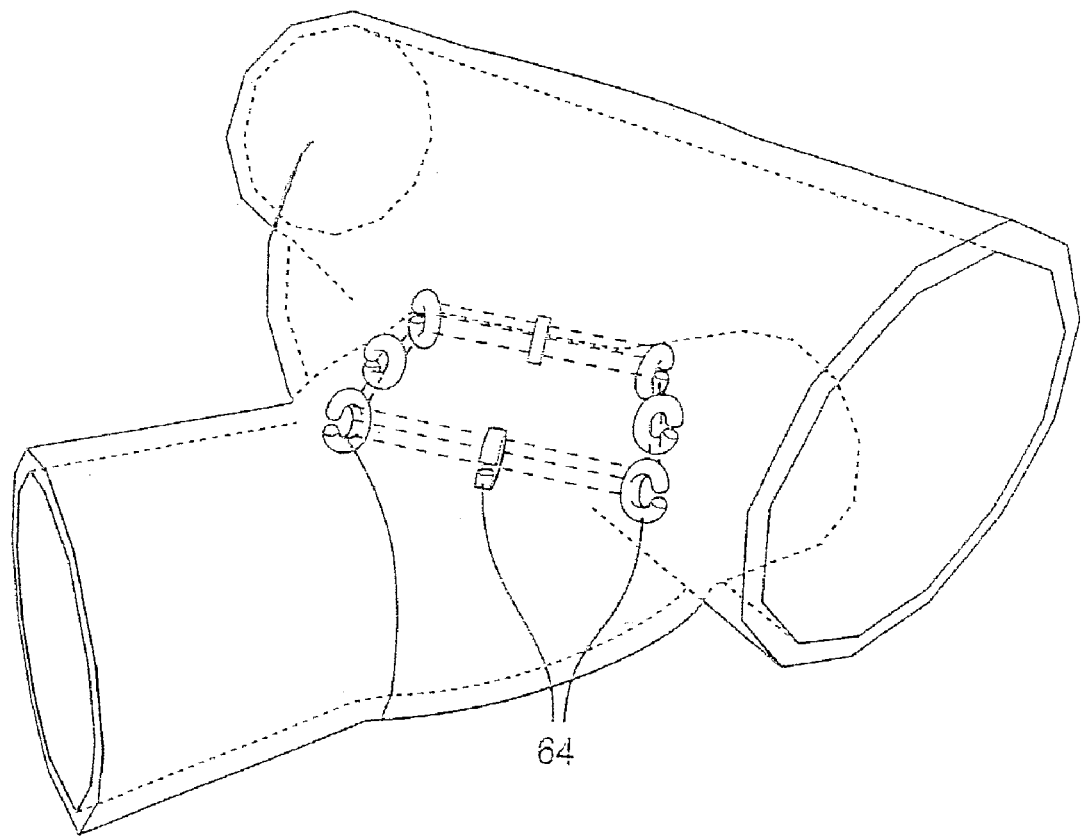

FIG. 41 is a highly schematic perspective view of blood vessels interconnected by side-to-side anastomose with loose staples.

FIGS. 1–6 show a first embodiment of a device for making anastomoses between hollow structures, in particular arteries or veins, by mechanical means.

In the present case, the device is a one-piece tubular or annular element 1, which is made of a biocompatible and plastically deformable material, for example a tantalum alloy or another material used in medical technology. Annular element 1 may be considered to be an assembly of two zigzag-like elongated elements 2 and 3 which extend substantially in circumferential direction but not along the contour line, which elements are interconnected at the facing vertices, thus forming a ring of diamond-shaped structures 4. Present on the vertices of the zigzag-like elements 2, 3 that face away from each other are pin-shaped elements 5, 6, which are provided with sharp tips 7 at their ends facing away from annular element 1, wherein the tips 7 of two associated pin-shaped elements 5, 6 forming a pair are directed towards each other. The pin-shaped elements may be straight, but also curved or angular, for example, thus forming staples which are C-shaped, as it were, whilst the pin-shaped elements may also be shaped more like lips.

Figure 1:
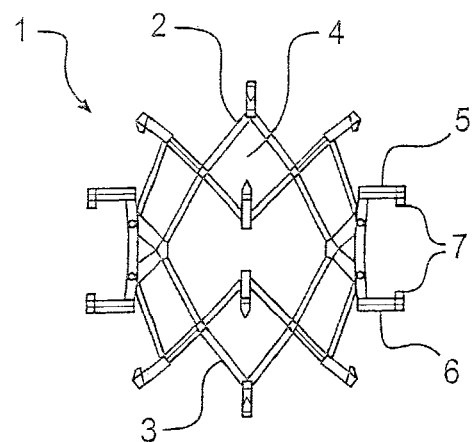
FIG. 1 is a perspective view of a first embodiment of the device for making anastomoses by mechanical means according to the invention, showing the starting position thereof.
Figure 2:
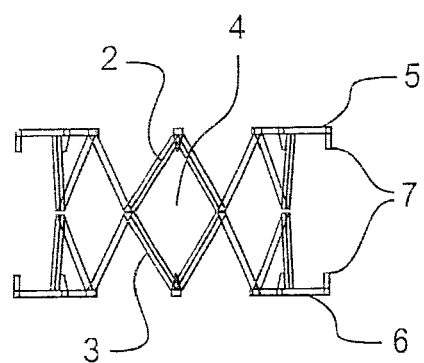
FIG. 2 is a side view of the device according to FIG. 1.
Figure 4:
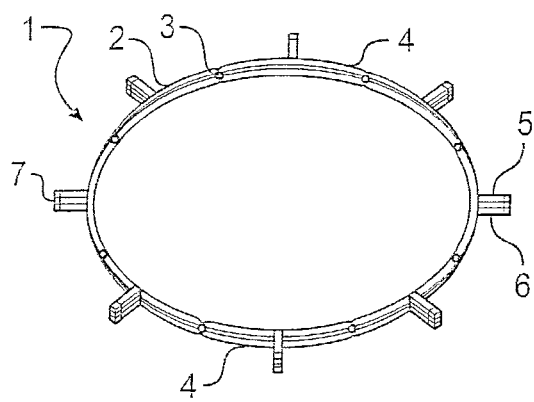
FIG. 4 is a perspective view of the device corresponding with FIG. 1, wherein the device is shown in the joining position, however.
Figure 5:
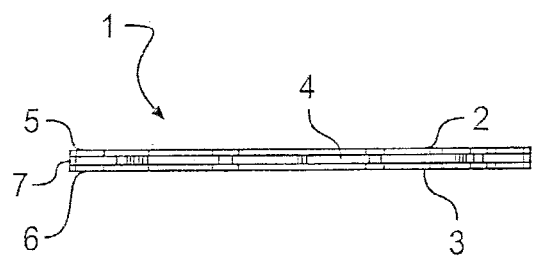
Figure 6:
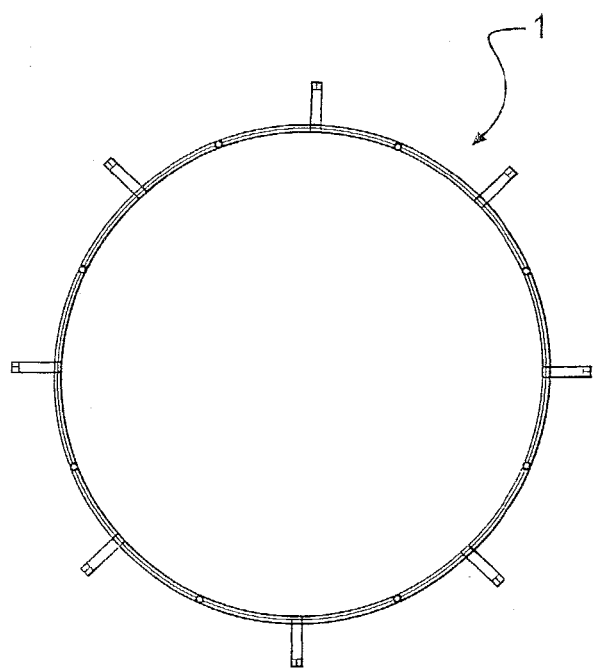
Figure 7:
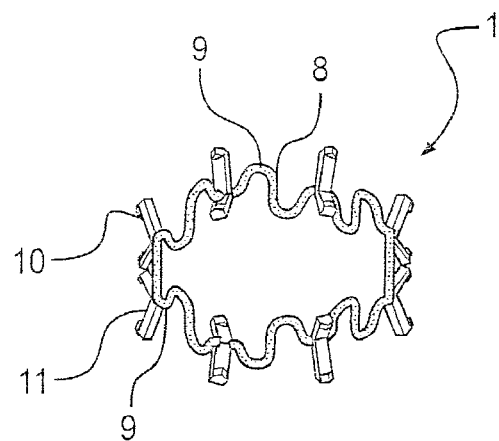
Figure 8:
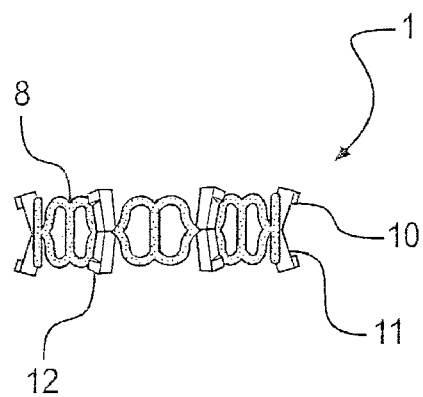
Figure 9:
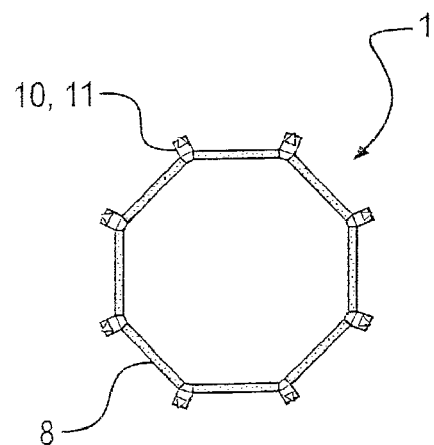
Figure 10:
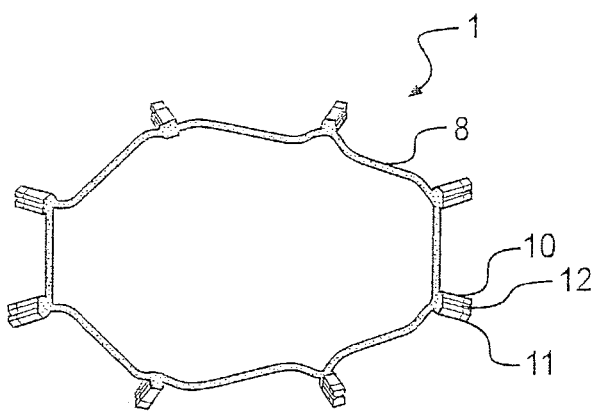
Figure 11:
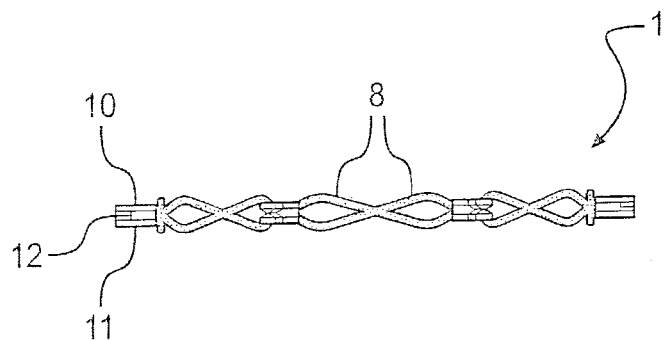
Figure 12:
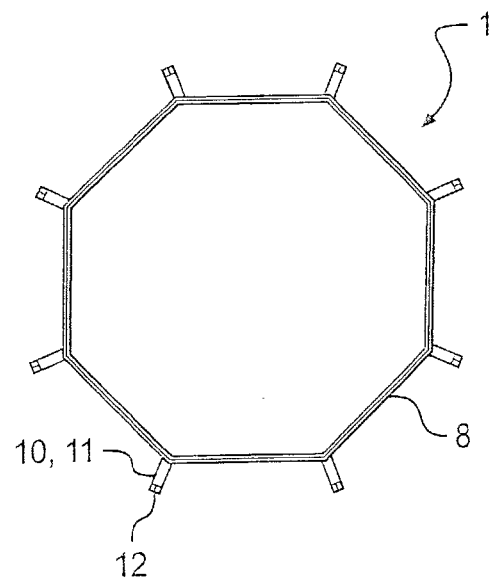

Since annular element 1 is formed from elongated elements 2, 3, whose length in circumferential direction is greater than that of annular element 1 in the position as shown in FIGS. 1–3, and since elements 2 and 3 are capable of deformation, it is possible to expand annular element 1 from the starting position as shown in FIGS. 1–3 to a final position, or joining position, as shown in FIGS. 4–6. In said joining position, annular element 1 has a diameter which is associated with a diameter which is at most equal to the length of elongated elements 2, 3. It would also be possible, of course, to expand annular element 1 only to a smaller diameter.

As is apparent from a comparison between FIGS. 4–6 and 1–3, the diamond-shaped structures 4 are deformed to a straighter shape, seen in circumferential direction, wherein the vertices comprising the pin-shaped elements 5, 6 have been moved closer together, such that the points 7 of pin-shaped elements 5, 6 of one pair engage each other. This movement of points 7 of pin-shaped elements 5 and 6 towards each other can be used for joining together or clamping together the walls of the hollow structures for the purpose of making the anastomosis, as will be explained in more detail hereafter.

Since the joining means in the form of pin-shaped elements 5, 6 comprising points 7 are automatically activated upon expansion of annular element 1 from the first starting diameter to the second, larger joining diameter, it is possible to use a very simple applicator, which consists of a shank-like element for insertion and manipulation, at the distal end of which a head is present, whose diameter can be enlarged. The head may therefore consist of an inflatable balloon, as is known from balloon catheters, or of a mechanically expandable head or the like.

In this embodiment, the following method is used for making an anastomosis.

In the case of a side-to-side anastomosis, incisions are made in the vessel to be bypassed and in the bypass at opposite locations. The applicator is inserted through the open free end of the bypass and passed through the incisions, possibly by means of a guide wire. Annular element 1 is thereby positioned so that one end of annular element 1 is positioned in one vessel and the other end of annular element is positioned in the other vessel, so that pin-shaped elements 5 and 6 are positioned on either side of the walls of the adjacent vessels. When expansion of the applicator causes annular element 1 to expand from the first starting diameter to the second, larger joining diameter, annular element 1 is radially enlarged on the one hand and axially shortened on the other end, wherein the pin-shaped elements 5 and 6 move together, eventually clamping down the walls of the vessels round the incisions, with points 7 becoming fixed in the walls of the vessels. The passage between the two vessels is determined by the diameter of annular element 1, so that said element functions both to keep the walls of the two vessels together and to keep the passage open. When annular element 1 has reached its joining position, the head of the applicator is reduced to a smaller diameter again and the applicator is withdrawn from the bypass lumen, after which the open end of the bypass is closed.

FIGS. 7–12 show a second embodiment of the device for making an anastomosis by mechanical means, wherein annular element 1 is a single, sinusoidal, elongated element 8, which expands in circumferential direction. Just like the elongated elements 2 and 3 of the first embodiment, the sinusoidal, elongated element 8 according to this second embodiment has a length dimension which is greater than the circumferential dimension of the annular element in the starting position thereof, and said length dimension of element 8 is at least equal to the circumferential dimension of the annular element in the joining position.

The sine shape of elongated element 8 is such that a number of vertices 9 is positioned centrally in annular element 1, seen in axial view, on which vertices 9 pin-shaped elements 10 and 11 are formed, with two pin-shaped elements 10, 11, which form a pair, being spaced apart at their free ends, seen in axial view, and meeting on elongated element 8 at their bottom ends. Pin-shaped elements 10 and 11 may be provided with a point or other projection 12 at their free ends, on facing sides, so as to be fixed in a vessel wall.

When said annular element 1 according to FIGS. 7–12 is expanded from the first starting diameter to the second, larger diameter, the ends of the pin-shaped elements 10, 11 of a pair are not automatically moved together, so that it will be necessary to use an applicator which is capable of closing the pin-shaped elements 10, 11 prior to, simultaneously with or after the expansion of annular element 1 so as to clamp down the walls of the adjacent vessels therebetween for making the anastomosis.

FIGS. 13–15 show an embodiment of an applicator which can be used for that purpose. The applicator is provided with a preferably rigid, shank-like element 13, on the proximal end of which means are provided for manipulating the applicator, such as a grip, and on the distal end of which a head 14 is formed. Head 14 is provided with two axially spaced-apart hubs 15, 16, one of which, for example hub 16, is capable of axial movement, which movement is controlled from the proximal end of shank-like element 13. Rigid arms 17 are arranged on hubs 15 and 16 in a star dike fashion, wherein pairs of associated arms 17 of the two hubs 15 and 16 present at corresponding circumferential positions are pivotally interconnected in a point some distance away from their free ends. Arms 17 are also pivotally connected to hubs 15 and 16, with the pivots extending tangentially with respect to shank-like element 13. In this manner clips are formed.

FIG. 14 shows that annular element 1 is placed on the head 14 of the applicator in such a manner that pin-shaped elements 10 and 11 are positioned between the free ends of arms 17, past a pivot 18, as a result of which the arms are pressed outwards from the position shown in FIG. 13 to the position shown in FIG. 15 upon movement of the hub, as a result of which elongated element 8 is straightened to a shape which extends more in circumferential direction, thereby enlarging the diameter, whilst the reduction of the angle between arms 17 of a pair of arms results in a reduced angle between pin-shaped elements 10 and 11, and the free ends of pin-shaped elements 10 and 11 are moved together, eventually clamping the two walls of the adjacent vessels between them. The placement and removal of the applicator is carried out in a manner which is comparable with the method described with reference to FIGS. 1–6.

FIGS. 16–21 show a third embodiment of the device according to the invention, which can be used for intraluminal placement in the case of a side-to-side anastomosis, but in particular also for extraluminal placement in the case of an end-to-side anastomosis.

In this case, annular element 1 consists of a circular, elongated element 19, which is circumferentially provided in a number of places with pin-shaped elements 20, which axially project to one side from said elongated element 19. The pins may be provided with points 21 thereby, whilst the pin-shaped elements 20 may be flat, or possibly round or the like. As is shown in FIGS. 19–21, the pin-shaped elements 20 are in large measure bent radially outwards in the joining position of the device, but they may also be bent tangentially.

In order to be able to deform the pin-shaped elements 20 from the starting position to the joining position, the applicator according to FIGS. 22–24 is provided. Also this applicator is provided with a shank-like element 13 and a head 14, but in this embodiment said head is provided with a detainer 23 in the form of a sleeve to be positioned proximally with respect to annular element 1, which is attached to the head, and with deflector elements 24, which can be moved at least axially, but preferably axially as well as radially, which deflector elements can be manipulated from the proximal end of shank-like element 13. Said deflector elements 24 consist of a fixed hub 25, an axially movable hub 26 and arms 27 which are pivoted together and connected to hubs 25, 26, which arms can be brought into engagement with the pin-shaped elements 20, and which can be deflected from an axial position to a radial position, wherein annular element 1 is stopped by detainer 23.

When the device according to FIGS. 16–21 and the applicator according to FIGS. 22–24 are used for making a side-to-side anastomosis, annular element 1 is placed intraluminally, and the pin-shaped elements 20 are passed through the vessel walls in places surrounding the openings that have been formed by incisions. When the pin-shaped elements 20 are subsequently bent radially outwards, it is no longer possible to remove annular element 1, because elongated element 19 is positioned inwardly of the wall of one vessel and the radially projecting pin-shaped elements 20 are positioned inwardly of the wall of the other vessel.

In the case of an end-to-side anastomosis, the annular element 1 is slid over the bypass. The bypass is everted round annular element 1 and the pin-shaped elements are passed through the wall of the bypass and through the wall of the vessel to be anastomosed (for example the aorta). Pin-shaped elements 20 can be deflected by extension of the deflector elements 24 of the applicator, and the walls will be fixed with respect to each other.

FIGS. 25–27 show a variant of the applicator according to FIGS. 13–15 which is suitable for placing an annular element 1 of a device of the type as shown in FIGS. 1–6 (shown at the bottom of FIGS. 25 and 27) or in FIGS. 7–12 (shown at the top of FIGS. 25 and 27). Also in this embodiment, a head 14 is attached to the shank 13 of the applicator. Said head 14 possesses a blunt end part 28 in this embodiment, which is fixed to shank 13 and also to a housing 29. The fixed connection between shank 13 and housing 29 is schematically illustrated by means of pin 30. A number of slots, eight in the illustrated embodiment, are circumferentially provided, in regularly spaced-apart relationship, in end part 28 and in housing 29. Said slots 31 are wide enough for receiving wedges 32, whereby it is important that slots 31 in end part 28 have the same angle of inclination as the distal front face 33 of wedges 32. Wedges 32 are radially held together by an elastic annular band 34. A control element 35 in the shape of a hollow shaft which can be slid over shank 13 comprises a bevelled front face 36 at the distal end, which is capable of cooperation with a complementary bevel 36' on the proximal end of wedges 32. The angle of inclination of bevel 36' and the front face 36 is smaller than that of the distal front face 33 of wedges 32.

An annular element 1 positioned in the applicator can be expanded from the starting position to the joining position by pressing wedges 32 outwards. This can be effected by moving control element 35 distally forwards, which control element presses wedges 32 outwards, via bevels 36', with its inclined front face 36, whereby the direction of the movement of wedges 32 corresponds with the direction of front faces 33 and the cooperating surfaces of end part 28. The combined axial and radial movement of wedges 32 causes the annular element surrounding wedges 32 both to expand radially and to be clamped together between the adjacent housing surface and the wedge surface, as a result of which pin-shaped elements 5, 6 and 10, 11 respectively of annular element 1 are moved together, clamping the vessel walls down between them. When control element 35 moves back, the elastic band 34 causes wedges 32 to return to the starting position. Thus, the applicator can be withdrawn from annular element 1 and be removed in a simple and reliable manner.

FIGS. 28–30 show a variant of the applicator according to FIGS. 22–24, which can be used in combination with an annular element 1 of the type according to FIGS. 16–21. The head 14 of this variant comprises a hollow shaft 37, with a blunt end part 38 present at the distal end thereof. Rectangular openings 39 (eight, for example) are provided in regularly spaced-apart relationship in the circumference of hollow shaft 37. Said hollow shaft 37 can move axially with respect to a housing 40, whose distal end surface 41 can serve as an anvil for annular element 1. Wedges 42 are placed in openings 39, which wedges are pivoted to the hollow shaft by means of resiliently flexible plates 43, in such a manner that wedges 42 can move outwards about a substantially tangential axis, from their starting position (FIG. 28) in openings 39 to a joining position (FIG. 30) in the direction of housing 40. Said movement is effected by moving a control element 44 in the form of a bar comprising a bevelled point 45 in forward direction, as a result of which the wedges are tilted outwards through 90°, in which joining position they are locked by the circumference of said control element 44. When housing 40 is moved axially forward with respect to hollow shaft 37, in the direction of wedges 42, the pin-shaped elements 20 of annular element 1 will come into contact with the wedges 42, and the pin-shaped elements 20 will be deflected outwards in a desired manner by the specially formed cavities 46 present in said wedges so as to fix annular element 1 of the device to the vessel walls. Wedges 42 will return to the starting position when control element 44 is withdrawn, and the applicator can be removed. In principle it would also be possible to effect direct deflection of pin-shaped elements 20 through expansion of wedges 42.

FIGS. 31–36 show another variant of an applicator, which can for example be used for inserting the device according to FIGS. 1–6 or 7–12. The applicator is therefore arranged for effecting a radial expansion of annular element 1 of the device and subsequently clamping together the joining means, such as pin-shaped elements 5, 6 or 10, 11, in axial direction or deforming them in some other manner. The difference with the preceding embodiments of the applicator is the fact that the embodiment according to FIGS. 31–36 is arranged for effecting the radial and axial deformations of the device in two separate steps. First the annular element 1 is radially expanded, and then the joining means are moved to their joining position. The advantage of this embodiment is the fact that the joining means are prevented from closing prematurely and thus missing part of the vessel wall.

In FIGS. 31–36, shank-like element 13, head 14 and detainer 23 can be distinguished. An end portion 47 having a convex end surface is formed on the distal end of shank-like element 13, whilst end part 47 is wedge-shaped or conical on proximal side 48. Besides shank-like element 13 and detainer 23, a third, relatively movable part 49 is provided, which can be moved both with respect to shank-like element 13 and with respect to detainer 23 from a control position outside the body. Part 49 and/or detainer 23 are circumferentially provided with a number of radially extending slots 50 for movably accommodating, at least in part, an equal number of arms 51. Arms 51 can move between the innermost starting position, in which they abut against a conical surface 52 of movable part 49, and an outermost joining position, in which they abut against the inner wall of detainer 23 (FIGS. 32, 33). Arms 51 comprise an outwardly curved deflection surface 53 near their distal ends, which is to mate with pin-shaped elements of annular element 1, which may be provided round arms 51, adjacently to deflection surfaces 53. An elastic band 54 (see FIGS. 35, 36) may extend through radial notches 55 present near the distal ends of arms 51, which band functions to cause arms 51 to spring back to an inward position.

As is shown in FIG. 34, it is also possible to use arms which are interconnected by an annular part 56 at their proximal ends instead of separate arms 51. This one-piece assembly may for example be in the form of a plastic moulding, whereby the pivoting movement of arms 51 is made possible by the elastic properties of the relatively long arms. Slots 50 are no longer required in this manner, since annular part 56 holds arms 51 in position.

The operation of the applicator is as follows. In the position as shown in FIG. 31, the applicator and the annular element 1 of the device, which is present thereon (not shown), are moved to their destination, and then the shank-like element 13 and the end part 47 are withdrawn in proximal direction with respect to part 49 (or part 49 is extended), and arms 51 are pressed radially outwards by the mating cooperation between the wedge-shaped proximal side 48 of end part 47 and the associated wedge-shaped surfaces of arms, because arms 51 are supported against a shoulder of part 49 (see FIG. 32). Annular element 1 is thereby deformed radially outwards by arms 51 to a larger diameter. Detainer 23 is then moved relative to shank-like element 13 and part 49, as a result of which the end face of detainer 23 is moved in the direction of the deflection surfaces and the joining means are deformed in such a manner that the vessel walls of the hollow structures are interconnected. When shank-like element 13 and part 49 are moved apart again, elastic band 54 will return arms 51 to their starting position as shown in FIG. 31.

Figures 37, 38:
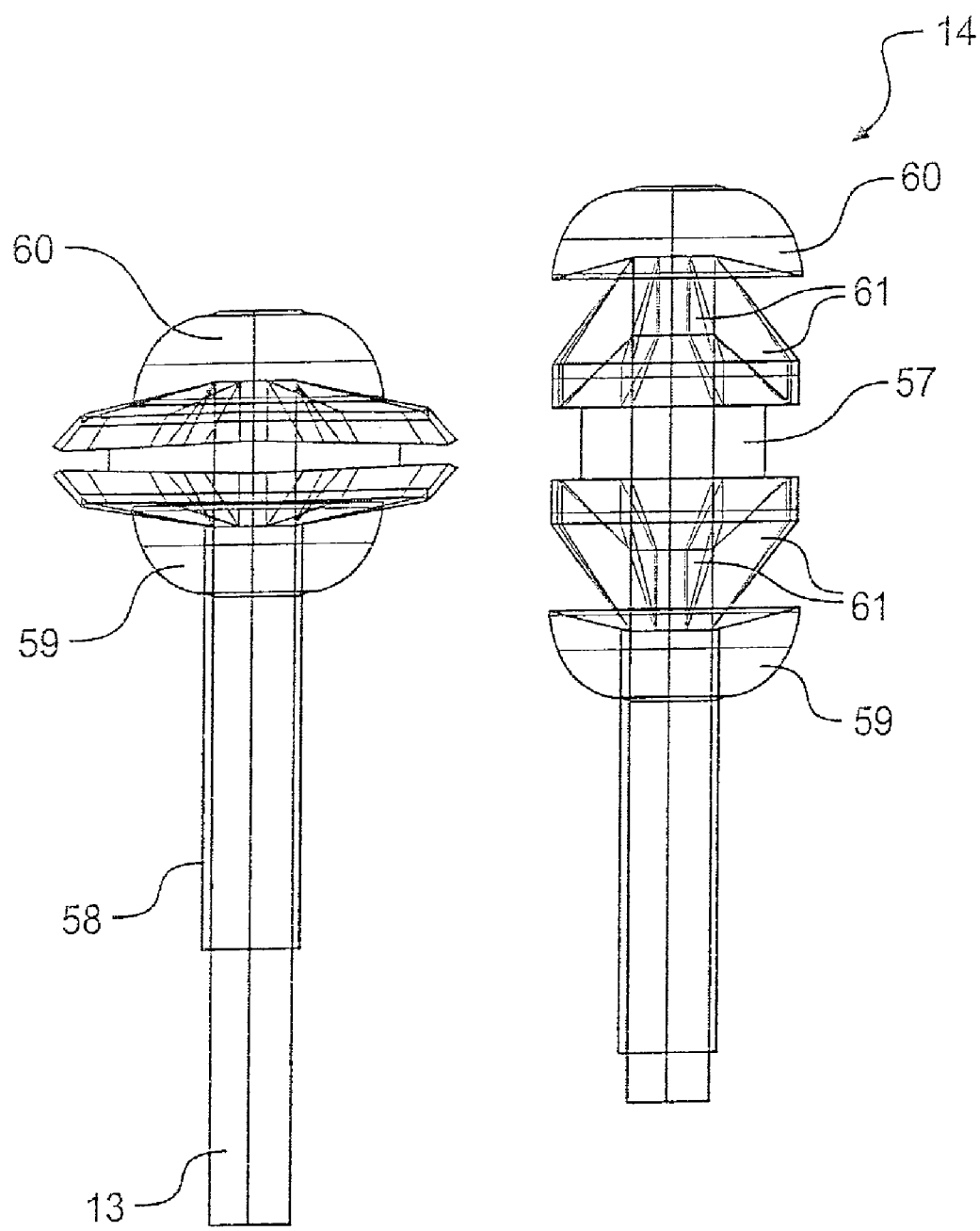
Figure 40:
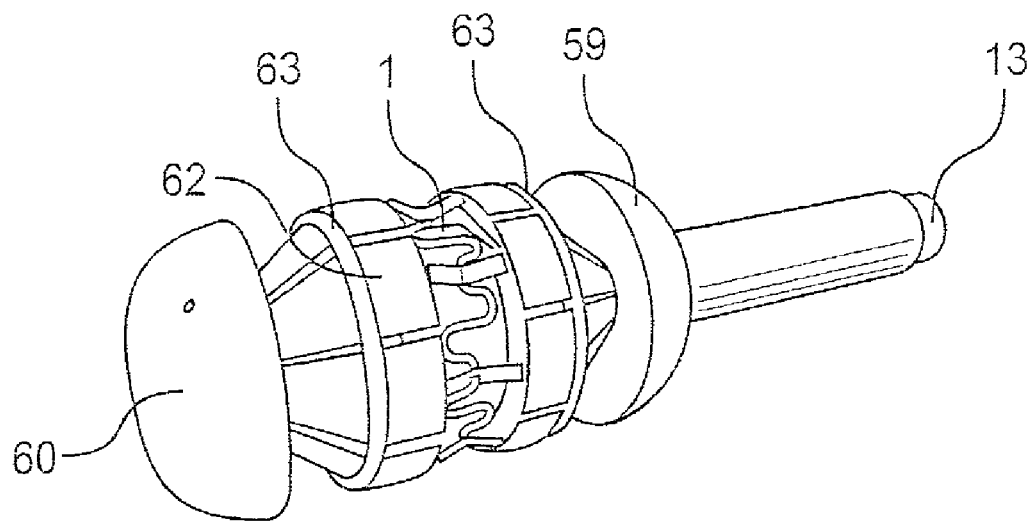
Figure 39:
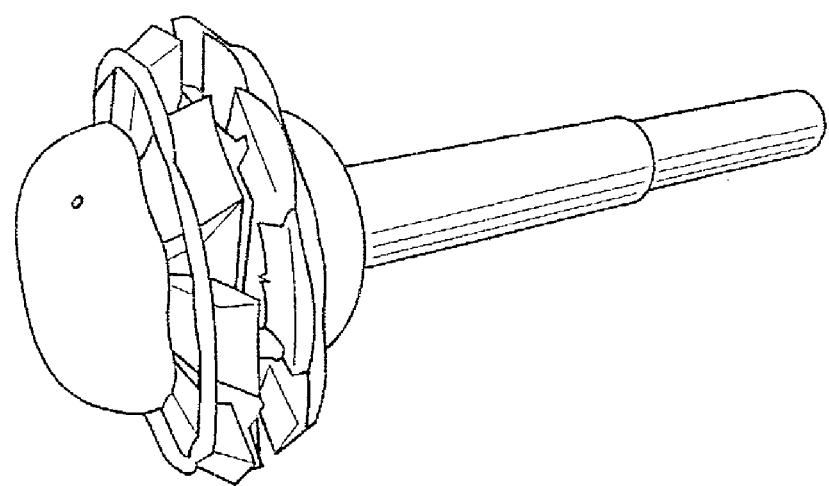

With the applicator according to FIGS. 37–40, the isovolumetric behaviour of some elastic and readily deformable material, such as rubber, is utilized for the radial expansion of annular element 1 of the device. The axial compression of the material will result in axial contraction and, if inward deformation is not possible, to radially outward expansion. In the illustrated embodiment, an isovolumetric core 57 is provided, on which annular element 1 of the device can be placed. Head 14 of said applicator furthermore comprises a sleeve 58 which is axially movable with respect to shank-like element 13, which sleeve comprises an end part 59 capable of cooperation with an end part 60 of shank-like element 13. Pivoted radial supports 61 are connected to the associated end parts 59, 60, they support circumferentially provided plates 62, which are held together by an associated elastic band 63, which also provides the return force. By moving the end parts 59, 60 together, the plates 62 are moved from the original sloping position as shown in FIGS. 38, 40 to an eventual joining position as shown in FIGS. 37,

39, wherein said plates extend practically perpendicularly to shank-like element 13. The facing surfaces of plates 62 are then capable of deforming the joining means upon further movement of end parts 59, 60 towards each other when the isovolumetric core 57 is compressed and the annular element is expanded thereby and, as already mentioned before, the joining means are moved to their joining position. This embodiment of the applicator is suitable for drastic miniaturisation.

FIG. 41 shows the result of a side-to-side anastomosis of two hollow structures, such as blood vessels, wherein loose staples 64 are used as joining means for the vessel walls. One of the above-described applicators may be used, providing that means are used for holding the staples 64 correctly spaced apart when said staples 64 are being inserted and moved to their joining position. Also in this embodiment the staples are placed intraluminally, whilst a guide wire may be used for moving the applicator to its correct position.

From the above it will have become apparent that the invention provides a system for making anastomoses between hollow structures by mechanical means, by means of which system an anastomosis can be made in a quick and reliable manner, as a result of which the negative effects of an anastomosis for the patient are minimized and the system is suitable for a large number of applications.

The invention is not limited to the above-described embodiments as shown in the drawing, which can be varied in several ways within the scope of the invention. Thus, the expandable version of the device might also be made of a resilient material or of a shape-memorizing metal, so that the device can move to the expanded position without external forces being exerted when the device is being provided. The elongated elements may not be recognizable as such, but they may be encountered in a different type of structure.

What is claimed is:

1. A system for connecting a first hollow structure to a second hollow structure, comprising:
    a connector including an annular or tubular element that is expandable from a first diameter to a second, larger diameter, and at least two deformable outer elements extending from the annular or tubular element; and
    an applicator having a proximal end; a distal end; a longitudinal axis; a movable element movable between at least a first position and a second position, the movable element configured to expand the connector from the first diameter to the second diameter when the connector is associated with the applicator when the movable element is moved from the first position to the second position; and a sleeve at least partially disposed about the movable element of the applicator, said sleeve being movable between a first position and a second position whereby the sleeve causes at least a portion of deformable elements of the connector to deform outwardly away from the longitudinal axis, and wherein said at least two deformable outer elements extend in a proximal direction when said connector is associated with said applicator.

2. The system of claim 1, wherein the connector further comprises at least two deformable inner elements extending from the annular or tubular element in a distal direction when said connector is associated with said applicator, and wherein at least a portion of the inner elements is deformable outwardly away from the longitudinal axis when said connector is associated with said applicator.

3. The system of claim 2, wherein the outer elements and inner elements are configured to clamp the first and second hollow tissue structures between the inner elements and the outer elements when the sleeve moves to the second position.

4. The system of claim 3, wherein the movable element comprises a plurality of arms that move from a first position to a second position to thereby expand the connector.

5. The system of claim 4, wherein each of the arms comprises a deflection surface at a distal portion thereof.

6. The system of claim 5, wherein each deflection surface is positioned such that when said movable element is in the second position, at least some of the inner and outer elements abut against said deflection surfaces during at least a part of said movement of said sleeve.

7. The system of claim 5, wherein each of said arms comprises a notch in a distal portion thereof, and the system further comprises an elastic band located in said notches.

8. The system of claim 5, wherein said arms are connected at a proximal portion by an annular part.

9. The system of claim 8, wherein said arms comprise a material with elastic properties.

* * * * *